US00PP32251P3

(12) United States Plant Patent
Hartman

(10) Patent No.: US PP32,251 P3
(45) Date of Patent: Sep. 29, 2020

(54) ***CALADIUM* PLANT NAMED 'BURST MY BUBBLE'**

(50) Latin Name: ***Caladium* X *hortulanum***
Varietal Denomination: Burst My Bubble

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 16/501,043

(22) Filed: Feb. 13, 2019

(65) Prior Publication Data

US 2020/0260628 P1 Aug. 13, 2020

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 6/00
See application file for complete search history.

*Primary Examiner* — Anne Marie Grunberg
(74) *Attorney, Agent, or Firm* — C. A. Whealy

(57) ABSTRACT

A new and distinct cultivar of *Caladium* plant named 'Burst My Bubble', characterized by its intermediate to tall height; upright and mounding plant habit; dense and bushy appearance; vigorous growth habit; rapid growth rate; fancy-type leaves that are dark green flushed with dark greyed purple in color with lighter greyed purple-colored spots; and leaf petioles that are light greyed red in color with numerous dark brown-colored stippling and streaks.

5 Drawing Sheets

Figure 1:
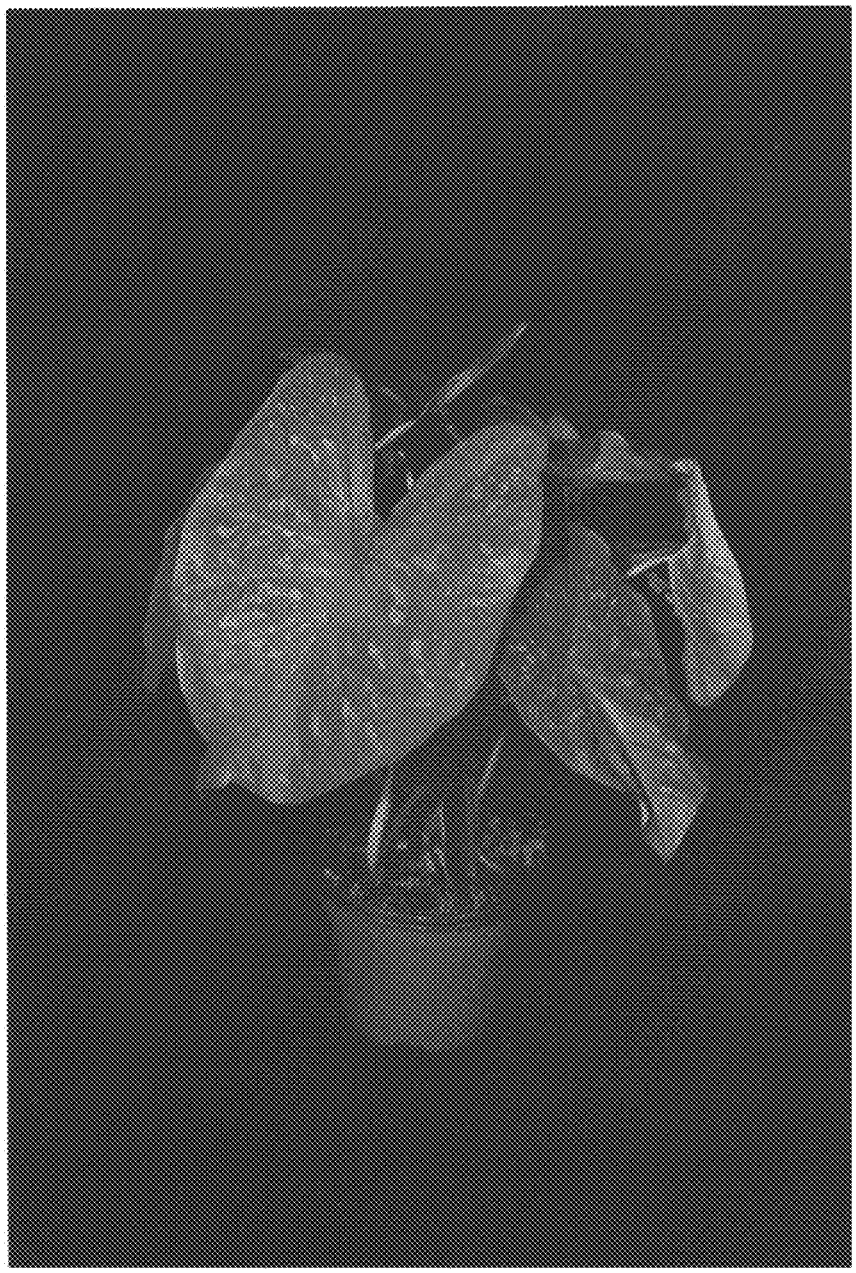

Botanical designation: *Caladium* X *hortulanum*.
Cultivar denomination: 'BURST MY BUBBLE'.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'Burst My Bubble'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2011 in Avon Park, Fla. of a proprietary selection of *Caladium* X *hortulanum* identified as code designation MH-1, not patented, as the female, or seed, parent with *Caladium* X *hortulanum* 'Red Flash', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2012.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2013 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Burst My Bubble'. These characteristics in combination distinguish 'Burst My Bubble' as a new and distinct *Caladium* plant:

1. Intermediate to tall in height and upright and mounding plant habit; dense and bushy appearance.
2. Vigorous growth habit and rapid growth rate.
3. Fancy-type leaves that are dark green flushed with dark greyed purple in color with lighter greyed purple-colored spots.
4. Petioles that are light greyed red in color with numerous dark brown-colored stippling and streaks.

Plants of the new *Caladium* differ primarily from plants of the female parent selection in the following characteristics:

1. Plants of the new *Caladium* have fancy-type leaves whereas plants of the female parent selection have lance-type leaves.
2. Plants of the new *Caladium* and the female parent selection differ in leaf color as leaves of plants of the new *Caladium* are dark green in color flushed with dark greyed purple in color with lighter greyed purple-colored spots whereas leaves of plants of the female parent selection are mostly salmon pink in color without any spots or markings.
3. Plants of the new *Caladium* and the female parent selection differ in leaf petiole color as petioles of the new *Caladium* are light greyed red in color with numerous dark brown-colored stippling and streaks whereas petioles of plants of the female parent selection are almost black in color or almost black and tinged with reddish orange.

Plants of the new *Caladium* differ primarily from plants of the male parent, 'Red Flash', in the following characteristics:

1. Plants of the new *Caladium* grow much faster than plants of 'Red Flash'.
2. Plants of the new *Caladium* and 'Red Flash' differ in leaf color as leaves of plants of the new *Caladium* are dark green in color flushed with dark greyed purple in color with lighter greyed purple-colored spots whereas leaves of plants of 'Red Flash' have red-colored venation and interveinal areas with pink and white-colored spots and dark green-colored borders.
3. Leaves of plants of the new *Caladium* typically have a metallic sheen whereas leaves of plants of 'Red Flash' do not have a metallic sheen.

Plants of the new *Caladium* can be compared to plants of *Caladium* X *hortulanum* 'Postman Joyner', not patented. In side-by-side comparisons, plants of the new *Caladium* differ primarily from plants of 'Postman Joyner' in the following characteristics:

1. Plants of the new *Caladium* grow much faster than plants of 'Postman Joyner'.
2. Plants of the new *Caladium* and 'Postman Joyner' differ in leaf color as leaves of the new *Caladium* are dark green in color flushed with dark greyed purple in color with lighter greyed purple-colored spots whereas leaves of 'Postman Joyner' are dark green in color with bright red-colored centers.
3. Leaves of plants of the new *Caladium* typically have a metallic sheen whereas leaves of plants of 'Postman Joyner' do not have a metallic sheen.
4. Plants of the new *Caladium* and 'Postman Joyner' differ in leaf petiole color as petioles of the new *Caladium* are light greyed red in color with numerous dark brown-colored stippling and streaks whereas petioles of 'Postman Joyner' are dark olive green to close to black in color.

Plants of the new *Caladium* can be compared to plants of *Caladium* X *hortulanum* 'John Peed', not patented. In side-by-side comparisons, plants of the new *Caladium* differ primarily from plants of 'John Peed' in the following characteristics:

1. Plants of the new *Caladium* grow much faster than plants of 'John Peed'.
2. Plants of the new *Caladium* and 'John Peed' differ in leaf color as leaves of the new *Caladium* are dark green in color flushed with dark greyed purple in color with lighter greyed purple-colored spots whereas leaves of 'John Peed' have dark red-colored centers and red-colored venation with dark green-colored margins.
3. Leaves of plants of the new *Caladium* typically have a metallic sheen whereas leaves of plants of 'John Peed' do not have a metallic sheen.
4. Plants of the new *Caladium* and 'John Peed' differ in leaf petiole color as petioles of the new *Caladium* are light greyed red in color with numerous dark brown-colored stippling and streaks whereas petioles of 'John Peed' are dark pink with dark green to almost black-colored stippling and streaks.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1 of 7) is a side perspective view of a typical plant of 'Burst My Bubble' in a container and grown in a shadehouse (tuber not de-eyed).

Figure 2:
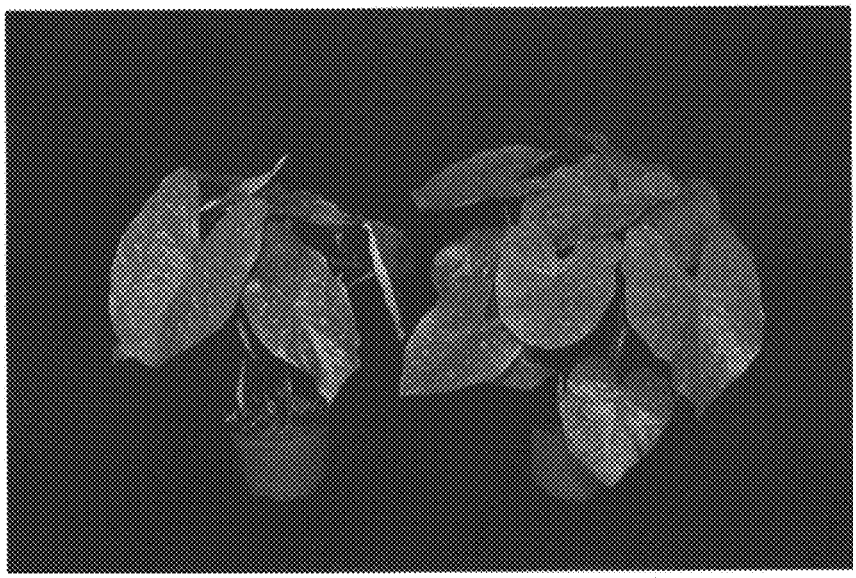

The photograph at the top of the second sheet (FIG. 2 of 7) is a comparison view of typical plants of 'Burst My Bubble' grown in containers; the plant on the left has not had its tuber de-eyed and the plant on the right has had its tuber de-eyed prior to planting.

Figure 3:
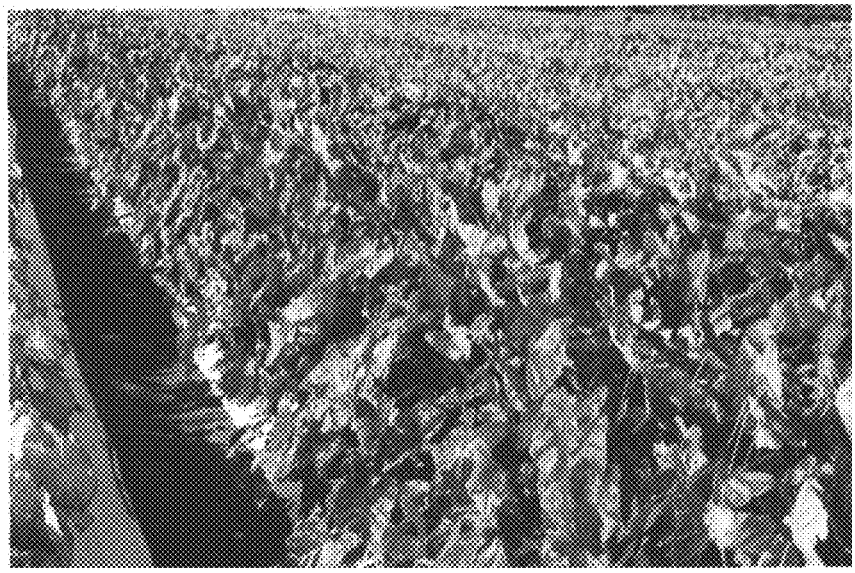

The photograph at the bottom of the second sheet (FIG. 3 of 7) is a side perspective view of typical plants of 'Burst My Bubble' grown in an open production field.

Figure 4:
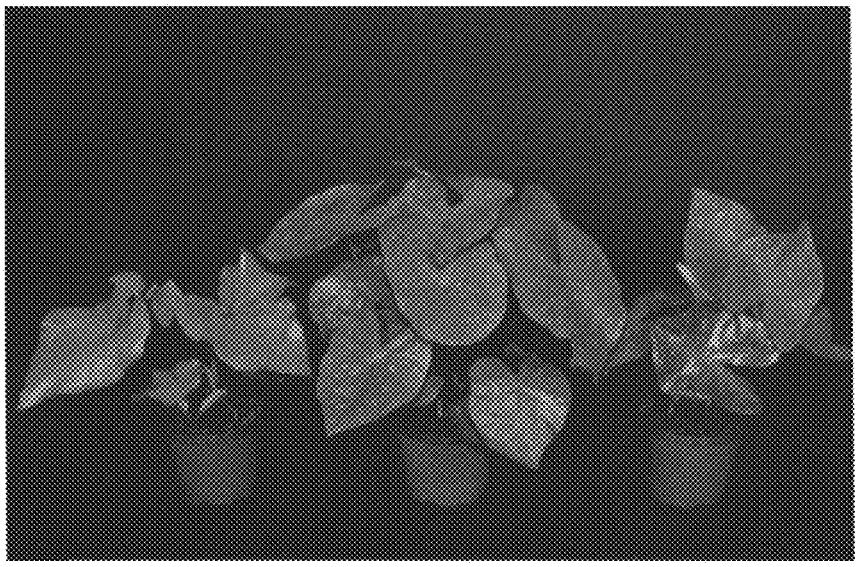

The photograph at the top of the third sheet (FIG. 4 of 7) is a comparison view of typical potted plants of the female parent selection (left), 'Burst My Bubble' (center) and the male parent, 'Red Flash' (right).

Figure 5:
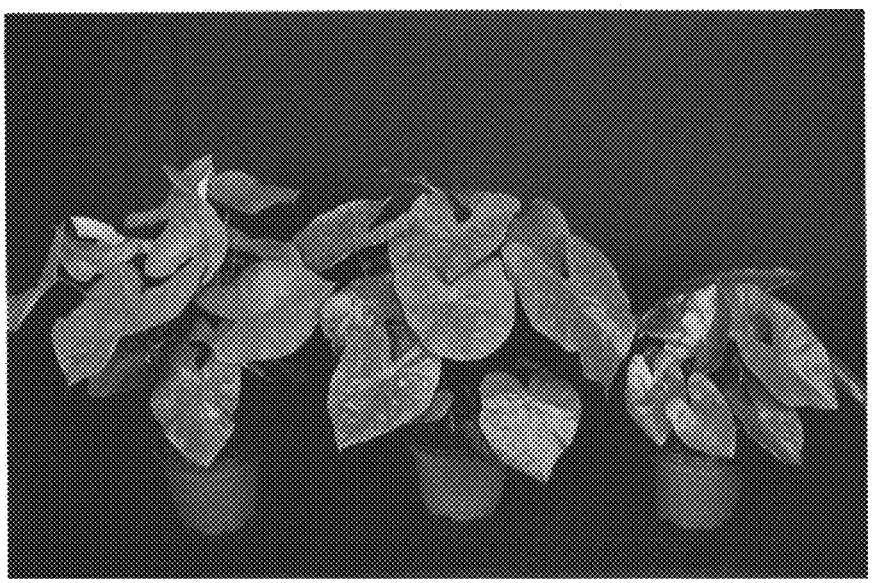

The photograph at the bottom of the third sheet (FIG. 5 of 7) is a comparison view of typical potted plants of 'Postman Joyner' (left), 'Burst My Bubble' (center) and 'John Peed' (right).

Figure 6:
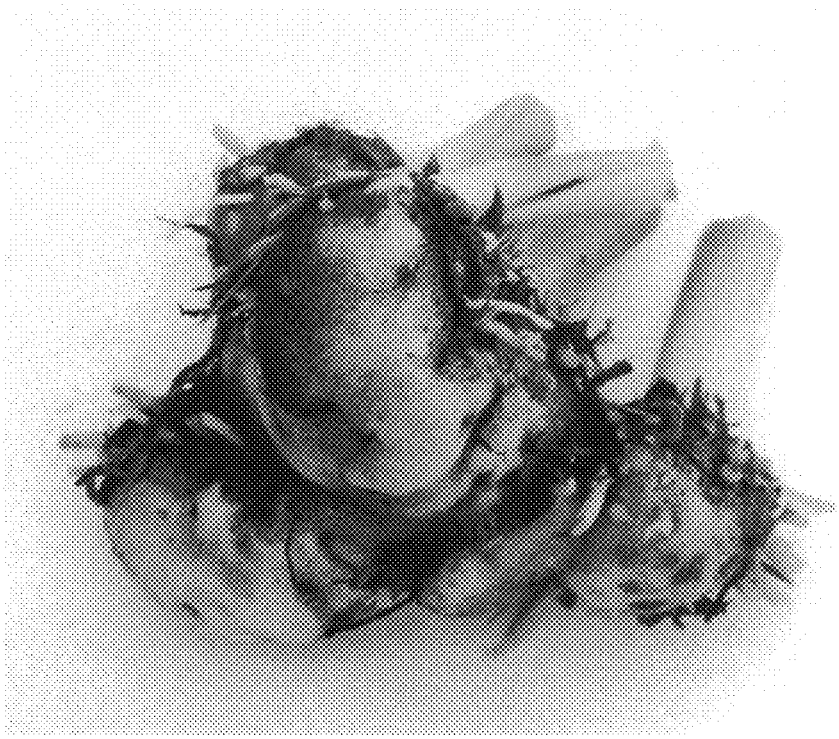

The photograph on the fourth sheet (FIG. 6 of 7) is a close-up view of typical freshly-harvested tubers with roots and leaf petioles of 'Burst My Bubble'.

Figure 7:
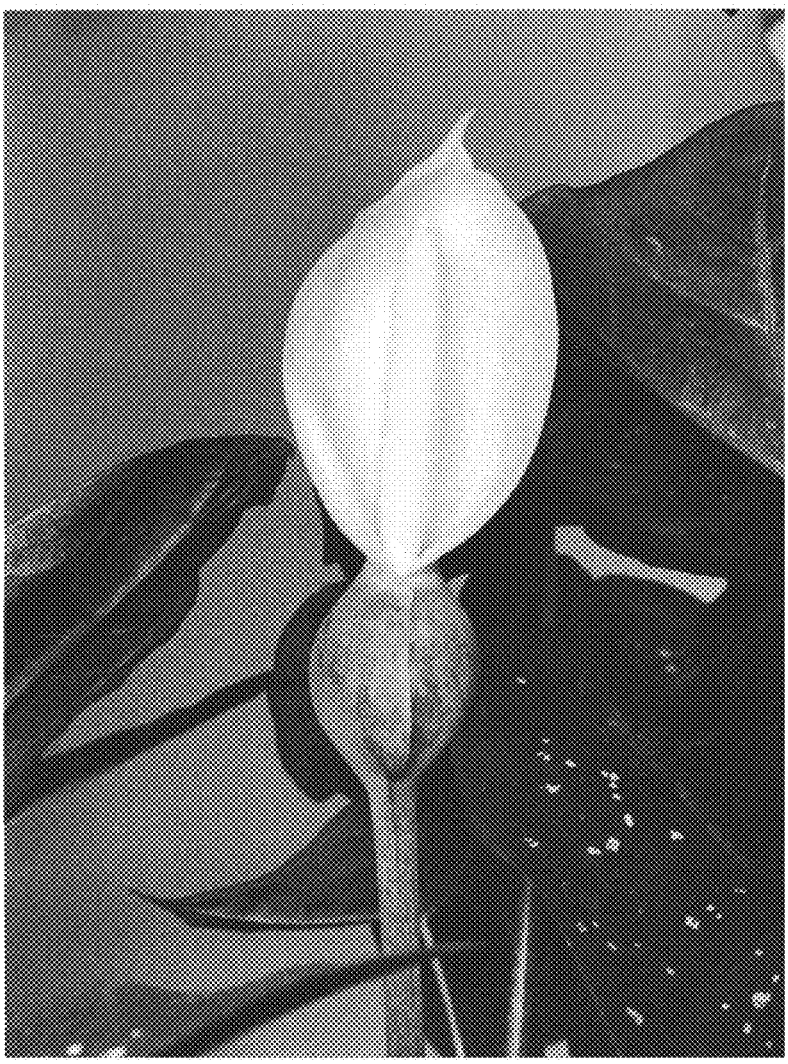

The photograph on the fifth sheet (FIG. 7 of 7) is a close-up view of a typical inflorescence of 'Burst My Bubble'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from 10,000 to 12,000 foot-candles. Plants grown in the shadehouse were eight weeks old and plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium* X *hortulanum* 'Burst My Bubble'.

Parentage:

*Female, or seed, parent.*—Proprietary selection of *Caladium* X *hortulanum* identified as code designation MH-1, not patented.

*Male, or pollen, parent.*—*Caladium* X *hortulanum* 'Red Flash', not patented.

Propagation:

*Type*.—By "chipping" the tubers.

*Time to initiate roots, summer*.—About seven to ten days at temperatures about 32° C.

*Time to initiate roots, winter*.—About two to three weeks at temperatures about 24° C.

*Tuber description* (*outdoor nursery-grown plants*).—Appearance: Multi-segmented; individual segments elliptic and irregular in shape. Height: About 3.5 cm. Diameter: About 5.9 cm to 8.5 cm. Segment height: About 2.8 cm. Segment diameter: About 2.8 cm. Axillary bud size: About 3 mm by 3 mm. Texture: Thick, starchy; somewhat brittle. Color: Epidermis, freshly-harvested: Close to 159D. Epidermis, dried: Close to 200A. Cortical tissue: Close to 2D and 4D. Axillary buds: Close to 36A and 37D. Root description: Thick, fleshy contractile roots with few lateral branches; color, close to N155D. Rooting habit: Medium density.

Plant description:

*Plant type*.—Herbaceous perennial; suitable as a potted plant in containers 15-cm to 25-cm and suitable as a landscape plant in shaded areas.

*Plant and growth habit*.—Intermediate to tall in height and upright to mounded plant habit; inverted triangle and wider than tall; dense and bushy appearance; vigorous growth habit and rapid growth rate; potted plants finish in saleable form in about six to seven weeks after planting tubers; leaf petioles and leaves arise from one or more growing points on tubers; leaf petioles initially upright and outwardly leaning with development.

*Plant height, from soil level to top of foliar plane, shadehouse-grown potted plants*.—About 30 cm to 34 cm.

*Plant height, from soil level to top of inflorescences, shadehouse-grown potted plants*.—About 40 cm.

*Plant diameter or spread, shadehouse-grown potted plants*.—About 40 cm to 46 cm.

*Number of shoots per plant, shadehouse-grown potted plants, tubers not de-eyed*.—About two to three develop per #1 tuber.

*Number of shoots per plant, shadehouse-grown potted plants, tubers de-eyed*.—About three to four develop per #1 tuber.

*Cataphylls, shadehouse-grown potted plants*.—Length: About 4.8 cm to 6.3 cm. Width: About 1.3 cm to 1.8 cm. Shape: Elongated elliptic. Apex: Acute or acuminate. Base: Sheathing the stem. Color, inner surface: Close to N155C and 182D; colors and patterns on the outer surface are visible on the inner surface. Color, outer surface: Close to 195B and 147C variably tinged with close to N170D; densely stripped, streaked and tessellated with close to 200A; with development, color becoming closer to N200A and 200B.

Leaf description:

*Arrangement and type*.—Alternate; simple; fancy-type.

*Length, shadehouse-grown potted plants*.—About 16 cm to 23.5 cm.

*Width, shadehouse-grown potted plants*.—About 12.6 cm to 17 cm.

*Shape*.—Ovate; mostly flat.

*Apex*.—Acute to acuminate.

*Base*.—Sagittate to peltate.

*Margin*.—Entire; mostly flat to somewhat undulate with broad undulations.

*Texture and luster, upper surface*.—Smooth, glabrous; when developing, glossy; with development, mostly dull typically with a metallic sheen.

*Texture and luster, lower surface*.—Smooth, glabrous; glaucous with a dull sheen.

*Venation pattern*.—Pinnate.

*Color, shadehouse-grown potted plants*.—Developing and fully developed leaves, upper surface: Background color: Darker than 139A flushed with 183A tinged with close to 53A. Leaf edge: Close to 185A; towards the margins, darker than 139A flushed with close to 183A tinged with 53A. Basal notch: Close to N186C. Midvein and primary venation: Close to N186A and N186B surrounded by close to 185A tinged with close to 46A. Random spots: Close to 184B and 184C. Developing and fully developed leaves, lower surface: Background color: Close to 191A tinged with close to 189A; random sectors, close to 187A to 187B. Leaf edge: Close to 183A; towards the margins, more green and darker than 189A. Basal notch: Close to 187A and N186C. Midvein: Close to 185D streaked and flecked with close to 184B. Primary venation: Close to 196A tinged, streaked and flecked with close to 184B. Random spots: Close to N170D and 182D.

*Petioles*.—Aspect: Initially upright and straight and outwardly leaning with development; flexible. Length, shadehouse-grown potted plants: About 24 cm to 30 cm. Diameter, distally, shadehouse-grown potted plants: About 3.5 mm to 5 mm. Diameter, proximally, shadehouse-grown potted plants: About 7 mm to 8 mm. Texture and luster: Smooth, glabrous; mostly glossy, distally, glaucous. Color, shadehouse-grown potted plants, when developing and fully developed: Close to 181D with dense stippling and streaks, close to 200A; distally (just below leaf junction), close to 182C to 182D and 147C with stippling and streaks, close to 182A. Wing length, shadehouse-grown potted plants: About 5.5 cm to 7.2 cm. Wing diameter, shadehouse-grown potted plants: About 9 mm. Texture and luster, inner and outer surfaces: Smooth, glabrous; dull to slightly glossy. Wing color, shadehouse-grown potted plants: Inner surface: Close to N155C and 182D; colors and patterns on the outer surface are visible on the inner surface. Outer surface: Close to N170D, 182D and 147C stippled, streaked and tessellated with close to 200A.

Inflorescence description:

Inflorescences observed on ten week-old shadehouse-grown potted plants.

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with mint and camphor notes.

*Natural flowering season and flower longevity*.—Plants of the new *Caladium* typically flower during the spring and summer in central Florida; flowers develop about ten weeks after growth commences; inflorescences last about three days before fading; inflorescences persistent.

*Spathe*.—Length, overall: About 11 cm. Length, distal open portion: About 7.5 cm. Length, proximal closed portion: About 3.5 cm. Width, distal open portion: About 5 cm. Depth, distal open portion: About 2 cm. Width, at constriction: About 1.2 cm. Width, proximal closed portion: About 2.7 cm. Shape, open portion: Elliptic. Apex: Cuspidate. Base: Acute. Margin: Entire; smooth; slightly recurved. Texture and luster, front surface: Smooth, glabrous; dull. Texture and luster, rear surface: Smooth, glabrous; dull; slightly glaucous. Color, front surface: Distal open portion: Close to 155C; with development, color becoming closer to 199B to 199C. Proximal closed portion: Close to 148C to 148D; towards the base, flushed with close to 187A; color does not change with development. Color, rear surface: Distal open portion: Close to 155C flushed with close to 145D; color does not change with development. Proximal closed portion: Close to 147C and 146B to 146C mottled and streaked with close to 185A, 184A and 187D; color does not change with development.

*Spadix*.—Length, overall: About 8.7 cm. Length, male flower zone: About 5 cm. Length, sterile zone: About 1.4 cm. Length, female flower zone: About 2.3 cm. Diameter, male flower zone: About 1 cm. Diameter, sterile flower zone: About 6 mm. Diameter, female flower zone: About 9 mm. Shape: Columnar, spindle-shaped. Apex: Acute. Base: Obtuse. Aspect: Upright. Color, mature, male zone: Close to 158D. Color, mature, sterile zone: Close to 158D. Color, mature, female zone: Close to N155D. Male flowers: Quantity per spadix: About 205. Shape: Obovate. Height: About 3 mm. Diameter: About 3.5 mm. Pollen amount: Abundant. Pollen color: Close to 10C. Female flowers: Quantity per spadix: About 160. Shape: Ovate to elliptic. Height: About 2.5 mm. Diameter: About 2.2 mm. Stigma color: Close to N155D. Ovary color: Close to 159C.

*Scape*.—Length: About 29 cm. Diameter: About 7 mm. Strength: Sturdy; flexible. Aspect: Mostly erect. Texture: Smooth, glabrous; distally, slightly glaucous. Color: Close to 181D densely stippled and streaked with close to 200A; distally, close to 182C to 182D and 147C stippled and streaked with close to 182A.

*Seeds and fruits*.—To date, seed and fruit development have not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'Burst My Bubble' as illustrated and described.

* * * * *